(12) United States Patent
Kato et al.

(10) Patent No.: US 10,610,325 B2
(45) Date of Patent: Apr. 7, 2020

(54) MEDICAL GUIDANCE APPARATUS

(71) Applicant: Canon U.S.A., Inc., Melville, NY (US)

(72) Inventors: Takahisa Kato, Brookline, MA (US); Luke McDonald Hydrick, Somerville, MA (US); Eric Penman Bogner, Lincoln, MA (US); Barret Daniels, Cambridge, MA (US); Hitoshi Nakamura, Boston, MA (US); Devashree Desai, Ashland, MA (US); Federico Perego, Milan (IT)

(73) Assignee: Canon U.S.A., Inc., Melville, NY (US)

(*) Notice: Subject to any disclaimer, the term of this patent is extended or adjusted under 35 U.S.C. 154(b) by 322 days.

(21) Appl. No.: 15/808,703

(22) Filed: Nov. 9, 2017

(65) Prior Publication Data

US 2018/0228568 A1 Aug. 16, 2018

Related U.S. Application Data

(60) Provisional application No. 62/460,025, filed on Feb. 16, 2017.

(51) Int. Cl.
*A61B 90/11* (2016.01)
*A61B 17/34* (2006.01)
(Continued)

(52) U.S. Cl.
CPC .......... *A61B 90/11* (2016.02); *A61B 17/3403* (2013.01); *A61B 34/10* (2016.02);
(Continued)

(58) Field of Classification Search
CPC ........ A61B 17/3403; A61B 2017/3405; A61B 2017/3407; A61B 2090/101; A61B 90/10; A61B 90/11; A61B 90/14
See application file for complete search history.

(56) References Cited

U.S. PATENT DOCUMENTS 4,841,967 A 6/1989 Chang et al.
5,047,036 A * 9/1991 Koutrouvelis ......... A61B 90/11
606/1
(Continued)

FOREIGN PATENT DOCUMENTS

EP 2567668 A1 3/2013
JP 2013059588 A 4/2013
(Continued)

*Primary Examiner* — Ryan J. Severson
(74) *Attorney, Agent, or Firm* — Canon U.S.A., Inc. IP Division

(57) ABSTRACT

A medical guidance apparatus includes a base assembly including a base ring having an inner circumference defining an opening; and a guide rotateably mateable with the base assembly, the guide including: a frame comprising: an inner circumference defining an opening; and an outer circumference, wherein, in a configuration where the guide is mated with the base assembly, the opening of the frame overlays the opening of the base ring; a gap extending from the inner circumference of the frame to the outer circumference of the frame; and an arc member including a first end integrally formed with the frame and a second end integrally formed with the frame, wherein the first end of the arc member is diametrically opposed to the second end of the arc member.

22 Claims, 9 Drawing Sheets

(51) Int. Cl.
  *A61B 90/00* (2016.01)
  *A61B 34/10* (2016.01)
(52) U.S. Cl.
  CPC . *A61B 2017/3407* (2013.01); *A61B 2034/107* (2016.02); *A61B 2090/067* (2016.02); *A61B 2090/0811* (2016.02); *A61B 2090/363* (2016.02); *A61B 2090/374* (2016.02); *A61B 2090/376* (2016.02); *A61B 2090/3762* (2016.02); *A61B 2090/3937* (2016.02); *A61B 2090/3945* (2016.02); *A61B 2090/3966* (2016.02)

(56) References Cited

U.S. PATENT DOCUMENTS

| | | | |
|---|---|---|---|
| 5,196,019 A | 3/1993 | Davis et al. | |
| 5,201,742 A | 4/1993 | Hasson | |
| 5,957,934 A | 9/1999 | Rapoport | |
| 6,119,032 A | 9/2000 | Martin et al. | |
| 6,185,445 B1 | 2/2001 | Knuttel | |
| 6,487,431 B1 | 11/2002 | Iwano et al. | |
| 6,505,065 B1 | 1/2003 | Yanof et al. | |
| 7,083,608 B2 | 8/2006 | Tomita et al. | |
| 7,187,104 B2 | 3/2007 | Yamamoto et al. | |
| 7,803,164 B2 * | 9/2010 | Gielen | A61B 17/3403 606/129 |
| 7,824,417 B2 | 11/2010 | Magnusson et al. | |
| 8,308,740 B2 | 11/2012 | Tolley et al. | |
| 8,511,316 B2 | 8/2013 | Boese et al. | |
| 8,603,078 B2 * | 12/2013 | Stefanchik | A61B 17/0218 600/102 |
| 9,125,676 B2 | 9/2015 | Sahni | |
| 9,192,446 B2 * | 11/2015 | Piferi | A61B 90/11 |
| 9,222,996 B2 | 12/2015 | Fujimoto et al. | |
| 9,408,627 B2 | 8/2016 | Sahni | |
| 9,433,390 B2 | 9/2016 | Nathaniel et al. | |
| 9,867,673 B2 * | 1/2018 | Onuma | A61B 90/11 |
| 10,226,300 B2 * | 3/2019 | Ng | A61B 34/20 |
| 10,274,553 B2 * | 4/2019 | Fujimoto | G01R 33/287 |
| 10,285,670 B2 * | 5/2019 | Arimitsu | A61B 5/055 |
| 2003/0055436 A1 | 3/2003 | Daum et al. | |
| 2004/0260312 A1 | 12/2004 | Magnusson et al. | |
| 2006/0229641 A1 | 10/2006 | Gupta et al. | |
| 2010/0063496 A1 | 3/2010 | Trovato et al. | |
| 2010/0082040 A1 | 4/2010 | Sahni | |
| 2011/0190787 A1 | 8/2011 | Sahni | |
| 2012/0022368 A1 | 1/2012 | Brabrand et al. | |
| 2012/0221036 A1 | 8/2012 | Ahmann et al. | |
| 2014/0022245 A1 | 1/2014 | Brannan et al. | |
| 2014/0275978 A1 * | 9/2014 | Fujimoto | G01R 33/287 600/422 |
| 2016/0038247 A1 | 2/2016 | Bharadwaj et al. | |
| 2016/0074063 A1 * | 3/2016 | Arimitsu | A61B 5/055 606/130 |
| 2017/0014200 A1 | 1/2017 | Onuma et al. | |
| 2018/0228568 A1 * | 8/2018 | Kato | A61B 17/3403 |

FOREIGN PATENT DOCUMENTS

| | | |
|---|---|---|
| JP | 2015-047303 A | 3/2015 |
| WO | 2008/047379 A2 | 4/2008 |
| WO | 2008/062474 A2 | 5/2008 |
| WO | 2008/062474 A3 | 5/2008 |
| WO | 2010/096149 A2 | 8/2010 |

* cited by examiner

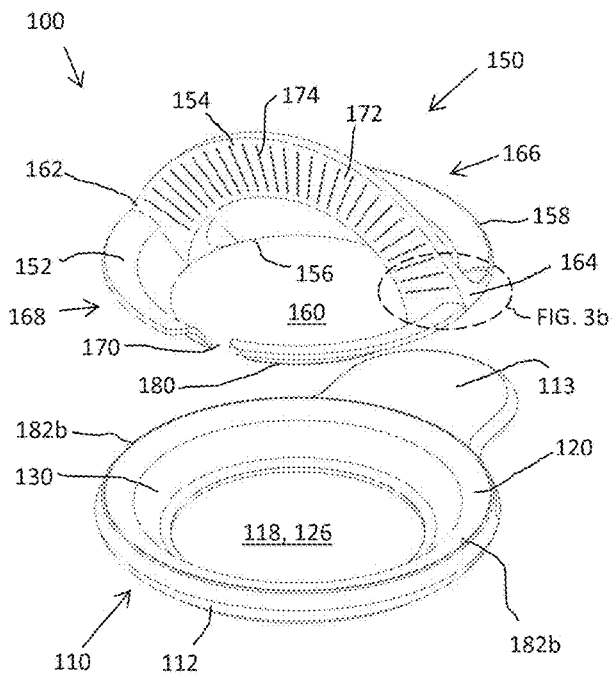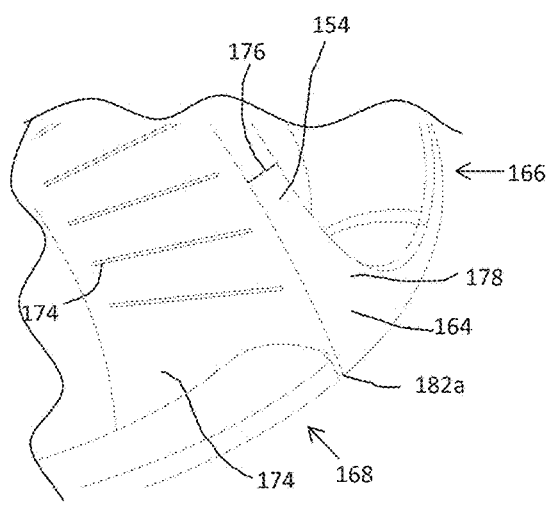
FIG. 3a
FIG. 3b
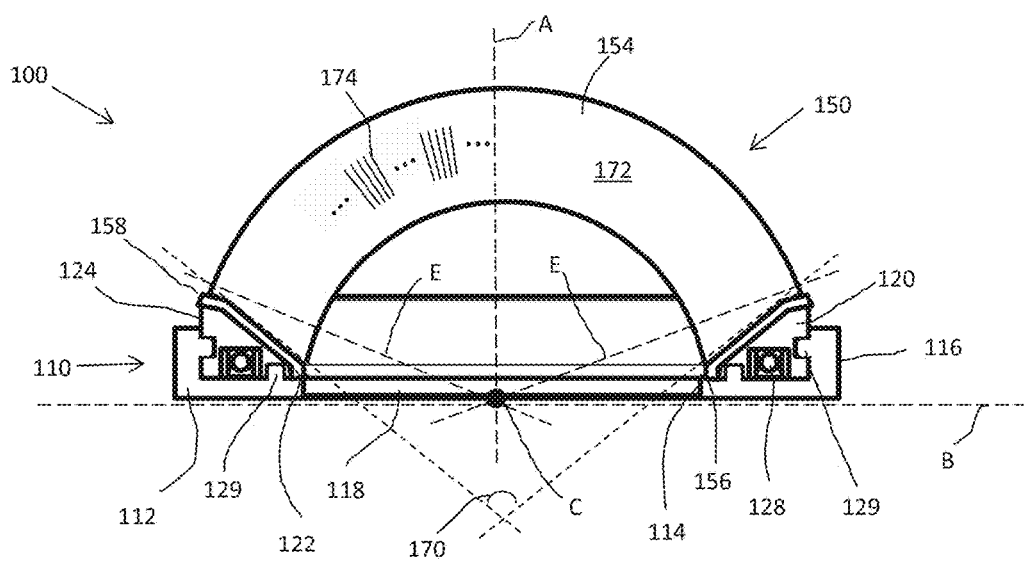
FIG. 4

MEDICAL GUIDANCE APPARATUS

CROSS-REFERENCE TO RELATED APPLICATIONS

This application claims priority to U.S. Provisional Application Ser. No. 62/460,025 filed Feb. 16, 2017, the content of which is incorporated herein by reference in its entirety.

FIELD OF THE DISCLOSURE

The disclosure of this application relates generally to medical devices, and in particular it relates to a medical guidance apparatuses for holding and positioning one or more medical instruments, and more particularly, to an apparatus suitable for minimally invasive puncture treatment.

BACKGROUND OF THE INVENTION

Percutaneous puncture treatment, in which a medical instrument, such as a needle, is guided to the affected part, is a typical example of minimally invasive treatment that is commonly performed. Examples of puncture treatments include ablation treatment in which a tumor or cancer cells are burned with radio waves and cryotherapy in which a tumor or cancer cells are frozen by using, for example, a freezing device or cooling gas. Puncture biopsy has also been commonly performed in pathological diagnosis based on tissue sampling.

In the medical environment, it is necessary to position a needle or multiple needles precisely inside tissue or a specific organ for accurate diagnosis or minimal invasive therapy. Biopsy, ablation, cryotherapy, aspiration and drug delivery are examples that require high precision needle placement and many of these treatments require the use of multiple needles in a treatment. Prior to a percutaneous incision, a target area of interest (e.g., tumor, nodule, etc.) is confirmed by means of non-invasive imaging with magnetic resonance imaging (MRI), ultrasound or other imaging modality. Once the target area of interest is positively determined, the clinician decides an entry point, inserting direction and depth to be reached by the needle. This process often requires a lengthy trial and error routine, which can be deleterious to the patient. Accordingly, in the last few decades there has been an increased interest in the development of needle guiding systems that can improve accuracy of needle positioning, minimize patient discomfort, and shorten time of operation.

To accurately position a needle with respect to a target, such as a tumor, in puncture treatment, an X-ray computed tomography (CT) unit, an MRI unit, etc., for acquiring medical images is used as a visualization unit for visualizing the needle. In puncture treatment in which such a modality is used as a visualization unit, it is often difficult to position the needle with respect to the target by a single puncturing process. Thus, the needle is generally guided to the target by acquiring medical images multiple times and correcting the insertion trajectory little by little in accordance with information from the acquired images. Accordingly, to reduce the operation time and burden on patients as well as patient's exposure to imaging radiation, various needle positioning apparatuses for positioning the needle to the target to provide a reduction in the number of times of corrections of the trajectory have been developed.

For example, U.S. Pat. No. 9,125,676 and U.S. Pat. No. 9,408,627 discloses a needle positioning apparatus having a cantilever arc guide structures with two ends attached to a base or support ring such that the guides are compliant against induced forces on both of the ends. The guides may experience large deformation forces during assembly. This assembly error in turn causes position inaccuracy. Furthermore, the guides have relatively low stiffness and do not maintain a precise position when subjected to force from the medical tool during guidance. Additionally, with respect to the apparatus of U.S. Pat. No. 9,125,676, a locking pin is used to maintain the arc guide perpendicular to the base plate. This causes large angle error because the fixing position is close to the triangle vertex of the angle, which increases an angular error with the small position error. Even when the locking pin is unlocked, the arc guide is free to rotate in the angular-error direction. Thus, whether locked or unlocked there is a large angular error. Also, the locking pin and fixing screws are small parts which are risky in a surgical context. Finally, the base plate of the U.S. Pat. No. 9,125,676 apparatus exposes the bearing surface for the arc guide to the external environment, which risks dust and fluid to enter during a medical procedure.

Thus, there is need for medical guide apparatus that avoids the above-noted problems.

SUMMARY OF EXEMPLARY EMBODIMENTS

A medical guidance apparatus according to some example embodiments comprises a base assembly including a base ring having an inner circumference defining an opening; and a guide rotateably mateable with the base assembly, the guide including: a frame comprising: an inner circumference defining an opening; and an outer circumference, wherein, in a configuration where the guide is mated with the base assembly, the opening of the frame overlays the opening of the base ring; a gap extending from the inner circumference of the frame to the outer circumference of the frame; and an arc member including a first end integrally formed with the frame and a second end integrally formed with the frame, wherein the first end of the arc member is diametrically opposed to the second end of the arc member.

A medical guidance apparatus according to some example embodiments comprises a base ring having an inner circumference defining an opening; a moveable ring having an inner circumference defining an opening, the moveable ring being rotateably coupled with the base ring; a rotary encoder; and a guide mateable with the moveable ring, the guide including: a frame comprising: an inner circumference defining an opening; and an outer circumference, a gap extending from the inner circumference of the frame to the outer circumference of the frame; and an arc member including a first end integrally formed with the frame and a second end integrally formed with the frame, wherein, in a configuration where the guide is mated with the moveable ring, the opening of the frame overlays the opening of the base ring and the opening of the moveable ring, and wherein the encoder is configured to measure an angular position of the moveable ring.

A method of guiding a medical tool according to some example embodiments comprises mounting a medical guidance apparatus onto a predetermined insertion point of a surface, the medical guidance apparatus comprising: a base assembly including a base ring having an inner circumference defining an opening; and a guide rotateably mateable with the base assembly, the guide including: a frame comprising: an inner circumference defining an opening; and an outer circumference, wherein, in a configuration where the guide is mated with the base assembly, the opening of the frame overlays the opening of the base ring; a gap extending from the inner circumference of the frame to the outer circumference of the frame; and an arc member including a first end integrally formed with the frame and a second end integrally formed with the frame, wherein the first end of the arc member is diametrically opposed to the second end of the arc member; positioning the guide to a predetermined position relative to the base ring; positioning the medical tool to a predetermined position along the arc member; and inserting the medical tool through the insertion point.

Further features will become apparent from the following description of exemplary embodiments with reference to the attached drawings.

BRIEF DESCRIPTION OF THE DRAWINGS

FIG. 3a is a partial exploded perspective view of the example medical guidance apparatus illustrated in FIG. 1.

FIG. 3b is a close-up perspective view of a portion of the example medical guidance apparatus illustrated in FIG. 3a.

FIG. 4 is a cross sectional view of the example medical guidance apparatus taken along line 4-4 of FIG. 2.

DESCRIPTION OF THE EMBODIMENTS

Figure 1:
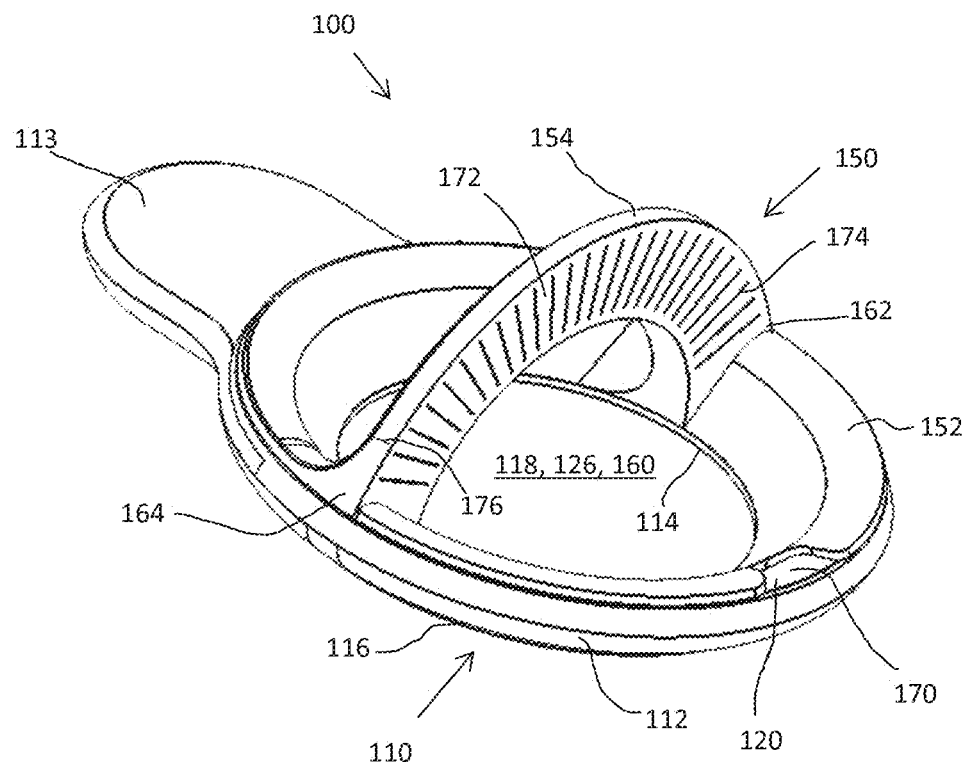
FIG. 1 is a perspective view of an example medical guidance apparatus in accordance with aspects of the disclosure.

In referring to the description, specific details are set forth in order to provide a thorough understanding of the examples disclosed. In other instances, well-known methods, procedures, components and materials have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description and/or illustration to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. The term "position" or "positioning" should be understood as including both spatial position and angular orientation.

Some embodiments of the present invention may be practiced in conjunction with a computer system that includes, in general, one or a plurality of processors for processing information and instructions, RAM, for storing information and instructions, ROM, for storing static information and instructions, a data storage device such as a magnetic or optical disk and disk drive for storing information and instructions, (e.g., an MRI image) an optional user output device such as a display device (e.g., a monitor) for displaying information to the computer user, and an optional user input device.

As will be appreciated by those skilled in the art, some aspects of the disclosure may be embodied, at least in part, as a computer program product embodied in any tangible medium of expression having computer-usable program code stored therein. For example, some aspects described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

Figure 2:
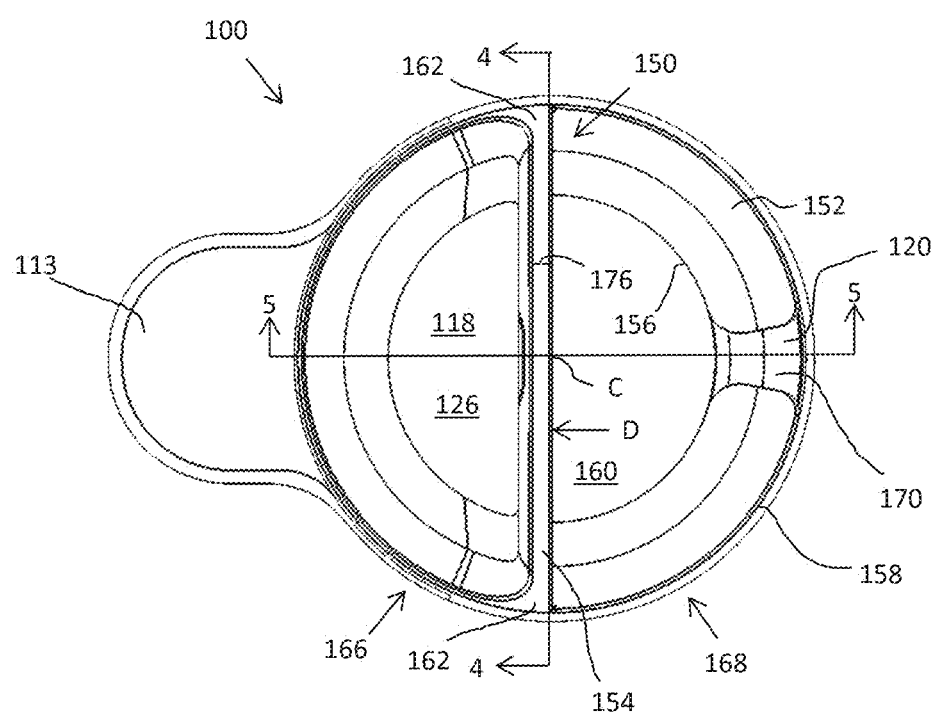
FIG. 2 is a top view of the example medical guidance apparatus illustrated in FIG. 1.
Figure 5:
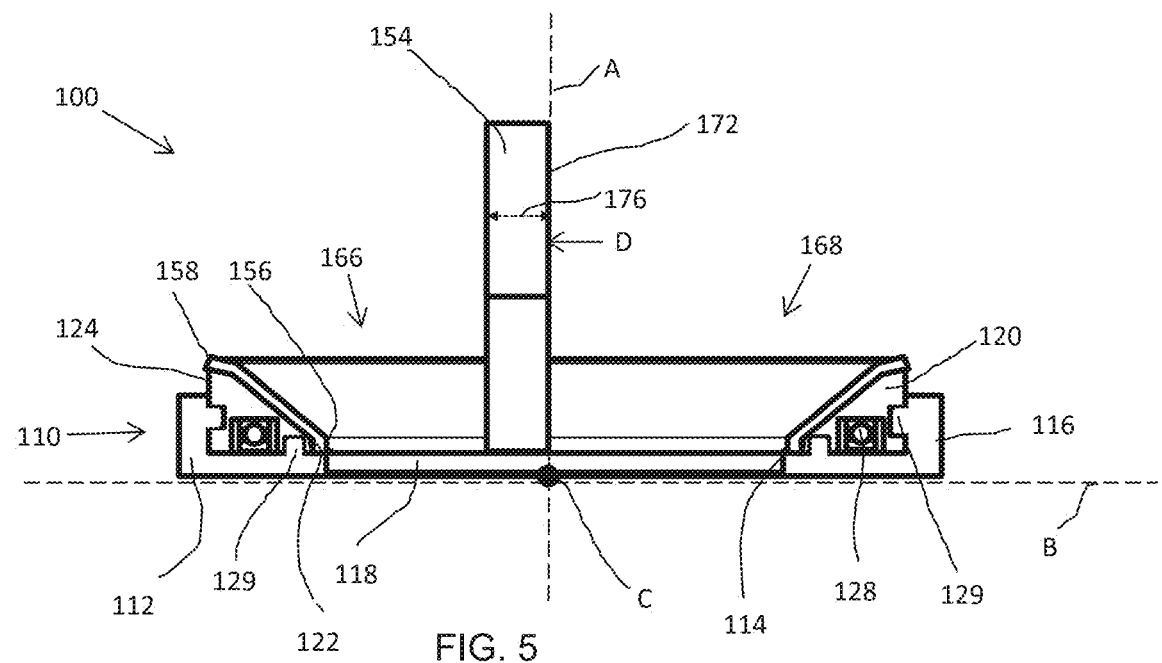
FIG. 5 is a cross sectional view of the example medical guidance apparatus taken along line 5-5 of FIG. 2.

FIG. 1 is a perspective view of a medical guidance apparatus too according to an example embodiment. FIG. 2 is top view of the medical guidance apparatus too. FIG. 3a is a partially exploded view of the medical guidance apparatus too. FIG. 4 is a cross section taken along line 4-4 of FIG. 2 and FIG. 5 is a cross section taken along line 5-5 of FIG. 2. The medical guidance apparatus too may generally include a base assembly 110 and a guide 150. The guide 150 may be rotateably mateable/coupleable with the base assembly 110. FIGS. 1 and 2 illustrate the guide 150 coupled with the base assembly 110. FIG. 3 illustrates the guide 150 removed from the base assembly 110. Further description of the guide 150 and the manner in which the guide 150 is coupled with the base assembly 110 is described in more detail below.

The base assembly 110 may include a base ring 112 in the form a ring shape having an inner circumference 114 and an outer circumference 116 (see FIGS. 4 and 5). The inner circumference 114 defines an opening 118. The opening 118 provides access to the patient when the medical guidance apparatus 100 is mounted onto a patient. That is, the opening 118 provides an area in which the patient's skin is exposed. The base ring 112 may also be referred to as a "fixed ring" or "stationary ring" because the base ring 112 is affixable to the patient and is not rotatable once affixed to the patient. The width of the base ring 112 (i.e., the distance from the inner circumference 114 to the outer circumference 116 in a radial direction, which is also the difference between the inner radius and the outer radius of the base ring 112), may be ⅙ to ½, more preferably ¼ to ⅓, the diameter of the opening. In one example aspect, the outer diameter of the base ring 112 may be from 50 to 150 mm (for example 80 mm) and the inner diameter (i.e., the diameter of the opening 118) may be 30 mm to 110 mm (for example 60 mm).

The base assembly 110 may further include a moveable ring 120. The moveable ring 120 is best seen in FIGS. 3a, 4, and 5. The moveable ring 120 may be in the form of a ring shape having an inner circumference 122 and an outer circumference 124. The inner circumference 122 defines an opening 126 that provides access to the patient. The width of the moveable ring 120 (i.e., the distance from the inner circumference 122 to the outer circumference 124 in a radial direction, which is also the difference between the inner radius and the outer radius of the moveable ring 120), may be ⅙ to ½, more preferably ¼ to ⅓, the diameter of the opening. In one example aspect, the outer diameter of the moveable ring 120 may be from 50 to 150 mm (for example 75) and the inner diameter (i.e., the diameter of the opening 126) may be 30 to 110 (for example 65). The moveable ring 120 may also be referred herein as a "rotatable ring" because the moveable ring 120 is capable of rotating about an axis A passing through a center point C. The center point C is the center of the circular opening 126 defined by the inner circumference 122. The axis A extends vertically through the center point C, i.e., perpendicularly relative to a horizontal plane B defining the surface to which the base assembly 110 may be mounted (see, e.g., FIGS. 4 and 5).

The moveable ring 120 may rotate relative to the base ring 112 via a bearing 128, as best seen in FIGS. 4 and 5. Thus, the base ring 120 may be referred to as a fixed ring because it is not rotatable, while the moveable ring 120 may be referred to as rotatable ring because it is rotatable relative to the base ring 120 via the bearing 128. The bearing may be a ball bearing or any other suitable bearing structure known in the art that allows for relative motion between two concentric rings. For example, the bearing may be a plain bearing, a roller bearing, and the like. As shown in FIGS. 4 and 5, the base assembly 110 may further include a seal 129. The seal 129 protects the bearing 128 by preventing contamination from the external environment from coming into contact with the bearing 128.

The base assembly 110 may further include a grip 113. The grip 113 may be attached to or integral with the base ring 112. The grip provides a mechanism for the operator to increase stability of the base assembly 110 during insertion of the medical instrument. Additionally, the grip 113 may house electronic components relating to the use of LED arrays, which is discussed below with respect to FIG. 9. The grip may also include visible markers for the medical images.

The guide 150 may comprise a frame 152 and an arc member 154. The frame 152 may have a ring shape similar to the base ring 112 and the moveable ring 124. The frame 152 may have an inner circumference 156 and an outer circumference 158. The inner circumference 156 defines an opening 160. The opening 160 provides access to the patient. The width of the ring shape of the frame 152 (i.e., the distance from the inner circumference 156 to the outer circumference 158 in a radial direction, which is also the difference between the inner radius and the outer radius of the frame 152), may be ⅙ to ½, more preferably ¼ to ⅓, the diameter of the opening. In one example aspect, the outer diameter of the frame 152 may be from 50 to 150 mm (for example 75 mm) and the inner diameter (i.e., the diameter of the opening 160) may be 30 to 110 mm (for example 65 mm).

As shown in FIGS. 1 and 3a, the arc member 154 may include a first end 162 and a second end 164. Each of the ends 162, 164 may connect to the frame 152 on diametrically opposed sides of the frame 152, thereby bisecting the frame 152 in a first 166 half and a second half 168 (best seen in FIG. 2). The frame 152 may include a gap 170 such that the second half 168 of the frame 152 is non-continuous. That is, the gap 170 serves as an interruption in the second half 168 of the frame 152. The gap 170 may be sized such that a medical instrument may pass through the gap 170 into opening 160 of the frame 152. The medical instrument can be an ablation probe in cryoablation, microwave ablation, radiofrequency ablation, laser ablation and irreversible electroporation ablation. Also, the medical instrument can be a needle-like device, for example biopsy needle, aspiration needle and drainage needle The gap 170 includes the width wide enough to get the medial instrument through for releasing/accepting. In other words, the gap 170 may extend from the inner circumference 156 to the outer circumference 158 of the frame 152 to provide a pathway for in instrument to exit the frame 152, as will be discussed below. The gap 170 may extend radially relative to the center of the opening 160 through the frame 152. The gap 170 may also extend non-radially (i.e., angled relative to the center of the opening 160). The first half 166 of the frame 152 may be continuous and lacking any gap. That is, from the point on the frame 152 where the first end 162 of the arc member 154 meets the frame 152 to the point on the frame 152 where the second end 164 of the arc member 154 meets the frame 152, the frame 152 is a continuous structure. In other words, the first half 166 of the frame 152 has a closed structure while the second half 168 of the frame 152 has a non-closed/open or interrupted structure.

The arc member 154 has an arc shape that spans an angle 170 relative to the horizontal plane B (see FIG. 4). The angle 170 may be from 60 to 170 degrees, more preferably 120 to 150 degrees. The arc member 154 may include a guide surface 172 that provides a guidance area for the instrument. The arc member 153 may include a plurality of angular reference marks 174 on the guide surface 172. The guide surface 172 may have a different color than the color of the surface on the opposite side of the arc member 154 (see also FIGS. 9 and 10). Having a different color allows the operator to quickly and easily ascertain which surface is the guide surface. This is particularly useful in an embodiment lacks the plurality of reference marks, as discussed below. The angular reference marks 174 signify an angle around center point C.

The use of the angular reference marks 174 is described below as part of a method of guiding a medical instrument is described below. The angular reference marks may be visible optically as well as in CT and X-ray images utilizing radio-opaque material. The radio-opaque material can be, but are not limited to, plastic including fillers of barium sulfate, bismuth subcarbonate, bismuth oxychloride, tungsten. The arc member 154 may have a thickness 176. The thickness 176 may be $1/15$ to $1/3$ the diameter of the opening 160, more preferably $1/12$ to $1/5$ the diameter of the opening 160, more preferably $1/10$ to $1/5$ the diameter of the opening 160. The ends 162, 164 of the arc member 154 may be integrally formed with the frame 152 such that the entire guide 150 is monolithically formed. That is, the entire guide 150 may be cast as a single piece of material. Additionally, as shown in FIG. 3b, each of the ends 162, 164 may include a fillet structure 178 on the side of the arc member 153 that transitions to the closed first half 166.

In some embodiments, the plurality of angular reference marks 174 on the guide surface 172 may comprise LED indicators. These LED indicators provide illumination of the guide surface or they may be turned on to indicate, for example, an angle of planned entry (e.g., a lit indicator appears at the planned entry angle). For medical guidance apparatus that is configured to detect the angle of a needle positioned in or near the medical guidance apparatus, the LED may be used to display when the needle is approaching or at a 'correct angle' by, for example, signaling with a green light at that angle.

Each of the monolithic structure of the guide 150, the closed structure of the first half 166 of the frame 152, the thickness 176 of the arc member 154, and the fillet structure 178 contributes to a structural advantage as compared to prior art devices. In particular, when force is applied to arc member 154 in a direction D against the guide surface 172 (see FIGS. 2 and 5), these structural features provide sufficient stiffness and rigidity to provide support and to minimize deflection, thereby providing sufficient support to the user when position an instrument. This structure, provides a high rigidity while the structure still provides an opening for needle egress. This is in contrast to a cantilever shape, i.e. an open frame, the monolithic structure has a greater stiffness and can withstand the forces associated with needle placement and maneuvering with smaller deflection. Further, the stiffness of the closed first half can be increased by increasing thickness of the closed first half while keeping the gap 170 in the second half 168.

Additionally, because of the monolithic structure, assembly error can be avoided. The structure of the guide 150 is able to provide this structural support despite having the gap 170 in the second half 168.

As best seen in FIG. 3a, the base assembly 110 and the guide 150 may each include corresponding taper portions 130, 180, respectively. The taper portion 130 of the base assembly 110 may be formed as part of the moveable ring 120 and may extend around the entire circumference of the moveable ring 120. The taper portion 180 of the guide 150 may be formed along the entire circumference of the frame 152. The two taper portions 130, 180 may be congruently formed such that taper 180 of the guide 150 geometrically fit within the taper portion 180 of the base assembly 110. By having a congruent geometry, guide 150 may easily mate with the base assembly via the taper portions 130, 180. In addition to allowing for easier mating, the taper provides greater range of angles for the reference marks 174 than as compared to a non-tapered configuration. Furthermore, the taper feature increases the structural rigidity of the arc member 154 against the force of the medical instrument imparted on the arc member 154 during guidance. In another aspect, when no moveable ring is present (discussed below), the taper portion of the base assembly may instead be formed in the base ring 112. In such an arrangement, the taper portion 180 is geometrically congruent with a taper portion of the base ring 112 in the same manner that the taper portion 180 may be geometrically congruent with the taper portion 130 of the moveable ring 120. In other words, the taper portions may be used to directly frictionally mate the guide 150 with the base ring 112. The amount of taper in the taper portion 180 is exemplified in FIG. 4, angle 170. However, the specific angle of the taper is not limiting. In some embodiments, the taper portions of the base assembly and guide 130 and 180 can be understood as a conical interface, where the base assembly 110 and guide 150 are geometrically aligned at the taper portions 130, 180 to the center axis of the conical interface. Kinematically, this interface eliminates in-plane relative motion between the base assembly 110 and guide 150 while allowing the guide 130 to rotate.

Figure 6:
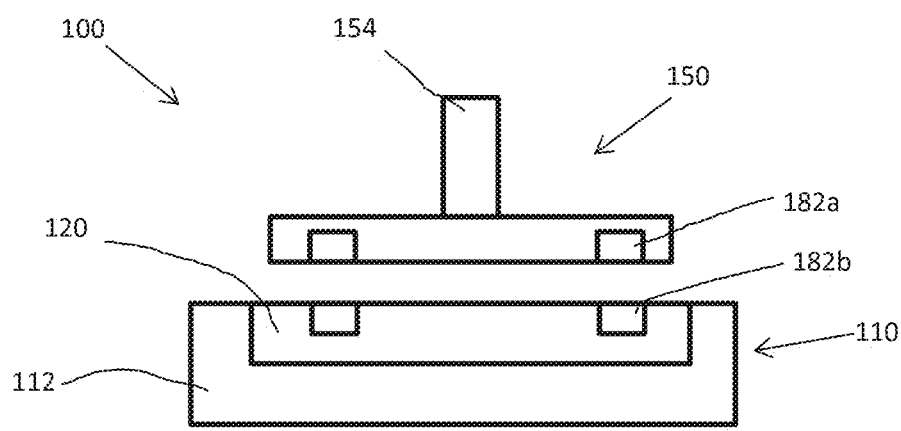
FIG. 6 is a schematic cross section of the example medical guidance apparatus illustrated in FIG. 1.

As noted above the guide 150 may be rotatably coupled with the base assembly 110. In one aspect, this may be achieved by mechanically coupling the frame 152 of the guide 150 to the moveable ring 120 via a mechanical interface. FIG. 6 illustrates a schematic cross-section representation of the principle of mechanically mating the guide 150 with the base assembly 110. As shown in FIG. 6, the guide 150 may include a first mechanical component 182a and the moveable ring 120 may include a second mechanical component 182b. The first and second mechanical components 182a, 182b together are the mechanical interface that allows for the coupling of the guide 150 with the moveable ring 120. The mechanical components may be any suitable mating structure such as corresponding male/female components, snap fitting, bayonet mount and Velcro-style fastener. and the like. One specific example of the mechanical interface is shown in FIGS. 3a and 3b. FIG. 3a shows the first mechanical component 182b and FIG. 3b shows the second mechanical component 182*a*. In this example, the first mechanical component 182*b* is a key, while the second mechanical component 182*a* is a keyway. While only one keyway is shown in FIG. 3*b*, a second keyway on the symmetrically opposite end of the arc member 154 would also be present to mate with the opposing key shown in FIG. 3*a*. The first mechanical component 182*b* (e.g., keys) may be configured to be aligned to a plane position of the guide surface 172. Also, as seen in FIG. 3*b*, the second mechanical component 182*a* (e.g., keyways) may include part of the guide surface 172. Accordingly, when mating the first mechanical component 182*b* (e.g., keys) with the second mechanical component 182*a* (e.g., keyways), the arc member 154 will have a predetermined orientation/alignment relative to the base assembly 110.

Once the guide 150 is mated with base assembly 110 via the moveable ring 120, the guide is able to freely rotate via the moveable ring 120. That is, the moveable ring 120 being rotatable about the axis A relative to the stationary base ring 112 (as described above), and the guide 150 being coupled with the moveable ring 120, allows the guide 150 and the moveable ring 120 to rotate together about the axis A when a rotational force is applied to either the moveable ring 120 or the guide 150.

Figure 7:
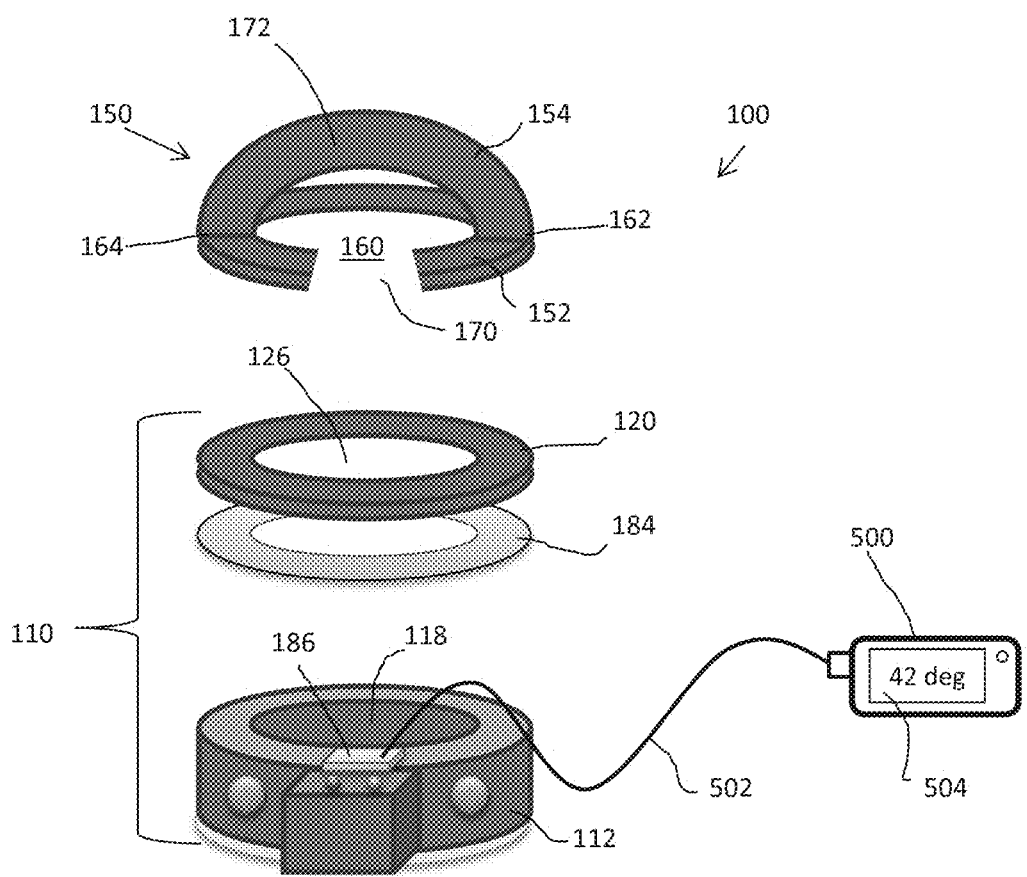
FIG. 7 is a schematic exploded perspective view of the example medical guidance apparatus illustrated in FIG. 1.

FIG. 7 illustrates an exploded schematic perspective view of the medical guidance apparatus 100 with additional features allowing for computer assisted positioning of the guide 150 relative to the base assembly 110. As shown in FIG. 7, the medical guidance apparatus 100 may further include a rotary encoder 184, 186. The rotary encoder may be any known device in the art device that converts angular position to an analog or digital signal. The rotary encoder may comprise a rotary scale 184 and a sensor head/sensor circuit board 186. The rotary scale 184 may be coupled with and/or integral with moveable ring 120 such that the rotary scale 184 can rotate with the rotatable ring 120. The sensor head faces the rotary scale 184, which is mounted on the rotatable ring 120, and is electrically connected to the sensor circuit board. The rotary encoder measures an angular position of the rotatable ring 120 against the base ring 112.

A controller box 500 may be electrically connecting to the medical guidance apparatus 100 via an electric cable 502. The controller box 500 may include an indicator 504, a microcontroller (not shown) and a power source (e.g., a battery) (not shown). The microcontroller may communicate with the sensor circuit board of the medical guidance apparatus 100. The sensor circuit board processes measurement signals of the angular position of the rotary scale 184 by the sensor head, and outputs the angular position to the microcontroller. The power source may power the indicator 504, the sensor circuit board, and the microcontroller. The indicator 504 may provide a number corresponding with the real-time rotational position of the moveable ring 120 as determined via the rotary encoder. The use of the rotary encoder to determine precise position of the moveable ring 120, and therefore the precise position of the guide 150 coupled with the moveable ring 120, allows for precise positing of the guide 150 about the A axis. In some embodiments, the use of a controller box to house one or more power sources is advantageous in that it keeps any field generated by the power source away from the patient. In such embodiments, any circuit not necessarily placed within the base unit may be located within the controller box as well.

In another aspect, the moveable ring 120 may be completely absent from the needle positing apparatus 100. In such an arrangement, the bearing 128 would also be absent.

In order to achieve relative rotational movement of the guide 150 relative to the base ring 112 in this configuration, the guide 150 may be rotationally mated with the base ring 112 via the above-described taper. Because the taper of the guide 150 would be geometrically congruent with the taper of the base ring 112, the guide may rest concentrically on the base ring 112 such that the underside surface of the guide 150 is contacting the topside surface of the base ring 112. Friction/gravity will allow the guide 150 to stay in place on the base ring 112. The rotation of the guide 150 is still possible because the guide 150 is not mechanically connected to the base ring 112, while the base ring 112 is fixed in place. Thus, the guide 150 may be rotated about the axis A by applying rotational force on the guide 150. In other words, the guide 150 may be rotated as an inner concentric ring flush against an outer concentric ring.

Figure 8:
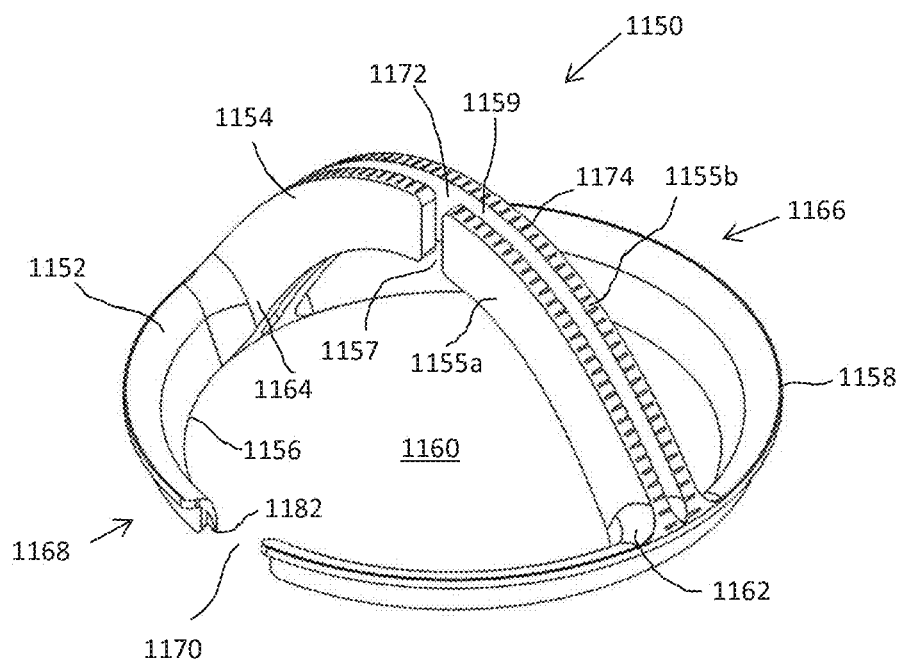
FIG. 8 is a perspective view of an example guide in accordance with aspects of the disclosure.

FIG. 8 illustrates a perspective view another embodiment of a guide 1150 for a medical guidance apparatus. The guide 1150 is similar to the guide 150 shown in FIGS. 1-3 and similar reference numbers represent corresponding features. Thus, the guide 1150 similarly may include a frame 1152, an arc member 1154, an inner circumference 1156, an outer circumference 1158, an opening 1160, a first end 1162, a second end 1164, a first half 1166, a second half 1168, a gap 1170, a guide surface 1172, a plurality of angular reference marks 1174, and an arc member thickness.

The width of the ring shape of the frame 1152 (i.e., the distance from the inner circumference 1156 to the outer circumference 1158 in a radial direction, which is also the difference between the inner radius and the outer radius of the frame 1152), may be the same as in frame 152. The arc member 1154 may have an arc shape that spans the same angle range as in the arc member 154. The arc member 1154 may be integrally formed with the frame 1152 such that the entire guide 1150 is monolithically formed, as with the guide 150. Thus, the guide 1150 has the same structural and assembly advantages noted above with the guide 150.

Similar to the guide 150, the guide 1150 may be rotatably coupled with the base assembly. The guide 1150 may be coupled via the same mechanical components noted above or with another mechanism such as the slot 1182 shown in FIG. 8. A corresponding feature may be present on the moveable ring or base ring to couple the guide 1150 to the base assembly. The guide 1150 may rotate in the same manner as the guide 150.

The difference between the guide 1150 and the guide 150 is provided in the arc member 1154. As shown in FIG. 8, the arc member of 1154 may comprise a first arc component 1155*a* and an opposing second arc component 1155*b*. The first and second arc components 1155*a*, 1155*b* have an arc shape and extend from the first end 1162 to the second end 1164 of the frame 1152. Each of the first and second components 155*a*, 155*b* may span the same angle range as each other, i.e., such that the first and second components 155*a*, 155*b* symmetrically oppose each other. Each of the of the first and second arc components 1155*a*, 1155*b* may include the angular reference marks 1174 formed on a topside of the components. Each angular reference mark 1174 on the first arc component 1155*a* corresponds with another angular reference mark on the second arc component 1155*b*. Having dual reference angular reference marks allows for easer visual alignment of the instrument with one set of opposing angular reference marks. The first arc component 1155*a* further includes a gap 1157 having sufficient size for the instrument to pass through the gap 1557. Additionally, the first arc component 1155*a* is separated from the second arc component 1155*b* by a gap 1559 sufficient size for the instrument to pass through the gap. Thus, an instrument is capable of passing first through the gap 1157 of the first arc component 1155a to enter the gap 1159 between the first and second arc components 1155a, 1155b. Once the instrument is located within the gap 1159 between the first and second arc components 1155a, 1155b, the instrument can be moved along the surface 1172 between the first and second arc components 1155a, 1155b. By signifying the guidance surface 1172 with two separated physical surfaces of the first and second arc components 155a, 155b, the medical instrument does not need to touch the parts. Therefore, the operator can insert the medial instrument with superior tactile feedback. Also, with space in between the first and second arc components 1155a, 1155b, the operator can easily adjust the medical instrument to be on the guide surface 1172.

Figure 9:
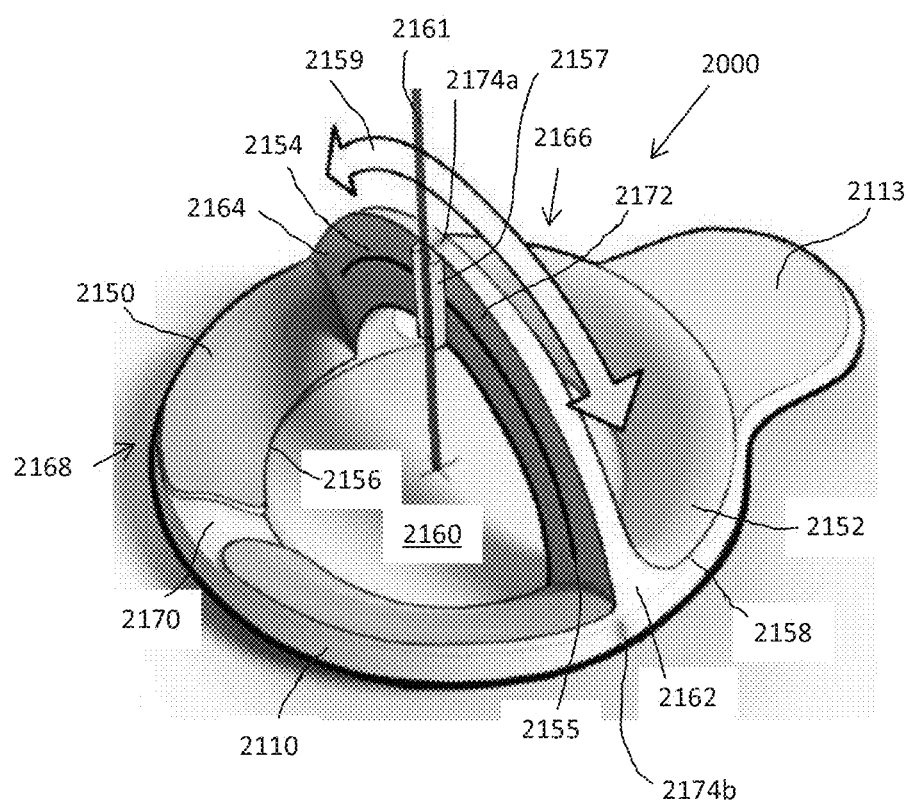
FIG. 9 is a perspective view of another example medical guidance apparatus in accordance with aspects of the disclosure.

FIG. 9 illustrates a perspective view another embodiment of a medical guidance apparatus 2000 having a guide 2150 and a base assembly 2110. The base assembly 2110 and the guide 2150 are similar to the base assembly 110 and guide 150 shown in FIGS. 1-6 and similar reference numbers represent corresponding features. Thus, the base assembly 2110 may similarly include a stationary base ring and a moveable ring. The guide 2150 similarly may include a frame 2152, an arc member 2154, an inner circumference 1156, an outer circumference 2158, an opening 2160, a first end 2162 and a second end 2164, a first half 2166, a second half 2168, a gap 2170, a guide surface 2172, and an arc member thickness.

The width of the ring shape of the frame 2152 (i.e., the distance from the inner circumference 2156 to the outer circumference 2158 in a radial direction, which is also the difference between the inner radius and the outer radius of the frame 2152), may be the same as in frame 152. The arc member 2154 may have an arc shape that spans the same angle range as in the arc member 154. The arc member 2154 may be integrally formed with the frame 2152 such that the entire guide 2150 is monolithically formed, as with the guide 150. Thus, the guide 2150 has the same structural advantage as noted above with the guide 150.

Similar to the guide 150, the guide 2150 may be rotatably coupled with the base assembly 2110. The guide 2150 may be coupled via the same mechanical components noted above or with another mechanism. A corresponding feature may be present on the moveable ring or base ring to couple the guide 2150 to the base assembly 2110. The guide 2150 may rotate in the same manner as the guide 150.

A difference between the guide 2150 and the guide 150 is provided in the arc member 2154. As shown in FIG. 9, the arc member of 2154 may comprise a rail 2155 and an instrument holder 2157. The rail 2155 may be formed in the guide surface 2172 and have an arc shape along the same arc path defined by the arc member 2154. The instrument holder 2157 may be slideable along the rail 2155 along the path shown by the arrow 2159. The instrument holder 2157 may be in the shape of a half cylindrical groove sized to receive an instrument 2161, for example a needle. The instrument holder 2157 may be shaped to fit other instruments, depending on the procedure being conducted. The instrument holder 2157 provides constrained guidance for the instrument 2161. The instrument holder 2157 can accurately guide the instrument 2161 by directing the half cylindrical groove to the target trajectory. Thus, the instrument holder 2157 can increase accuracy and can reduce intervention.

The instrument holder 2157 may be shaped to fit multiple instruments in a pre-set geometric configuration, for example multiple cryo-ablation needles arranged so the two or more needles will be held by the instrument holder 2157. For example, two needles may be held simultaneously, both positioned near the arc member 154 or tangential to the arc member. In other examples, three, four, or more needles may be held simultaneously by the instrument holder 2157 in a triangle, square, diamond, etc. configuration. The instrument holder 2157 may provide constrained guidance for the instruments to maintain the geometric relationship between instruments (e.g., parallel insertion) during the procedure.

Another difference shown in FIG. 9 is the use of illumination indicator 2174a in place of physical marks used in the other example embodiments. That is, as seen in FIG. 9, there are no line marks as in the above-described embodiments. Rather, as shown in FIG. 9, the illumination indicator 2174a may be placed along the topside of the arc member 2154. The illumination indicator 2174a may serve the same function of the marker discussed above. While one illumination indicator 2174a is shown on the arc member 2154 (because only one is lit up), there may be a plurality of illumination indicators along the entire span of the arc member at the same intervals of the hatch marks shown in the other example embodiments. Only one illumination indicator will be lit up during use to show the operator where the instrument should be placed along the arc member. Thus, the illumination indicator 2174a in FIG. 9 is showing the current desired position of the instrument. With the illumination indictor, rather than the operator needing to visually find a particular marker along the arc, the operator can easily and quickly see where to place the instrument along the arc. Another illumination indicator 2174b may be provided on the outer circumference of the base ring. The illumination indicator 2174b may serve the same function as the other illumination indicator with regard to the desired rotational position of the guide 2150. The illumination indicator 2174b may indicate the insertion plane (see FIG. 15 and below discussion). Accordingly, the illumination indicators with respect to the base ring may also be present along the entire circumference, while only a single indicator is illuminated in the example shown in FIG. 9. Thus, because the operator does need to read the angular reference marks, the duration of the intervention as well as mental stress of the operator is reduced. The illumination indicators may be an LED array for which the electronics to electrically drive the array are stored in a grip 2113. It should be understood that the illumination indicators may be applied to any of the other example embodiments disclosed herein. That is, the illumination indicators is not a mutually exclusive feature and can be used in place of or in alongside the hatch marks. The guide surface 1172 and/or the entire second half 2168 of the frame 2152 may be a different color than the side of the arc member opposite the guide surface and/or the first half 2166 of the frame 2152.

Another optional feature of some embodiments that is illustrated in FIG. 9 is a differentiating marker located on the guide 2150. The differentiating marker is show as a different color or hue located on the surfaces of the guide 2150 visible during use. This differentiates the portion of the medical guidance apparatus where the needle will be placed and guided. The differentiating marker may be, for example, a different color, an adhesive, a pattern, or some other differentiator that the physician can use to quickly differentiate which portion of the device should be used during needle placement.

Figure 10:
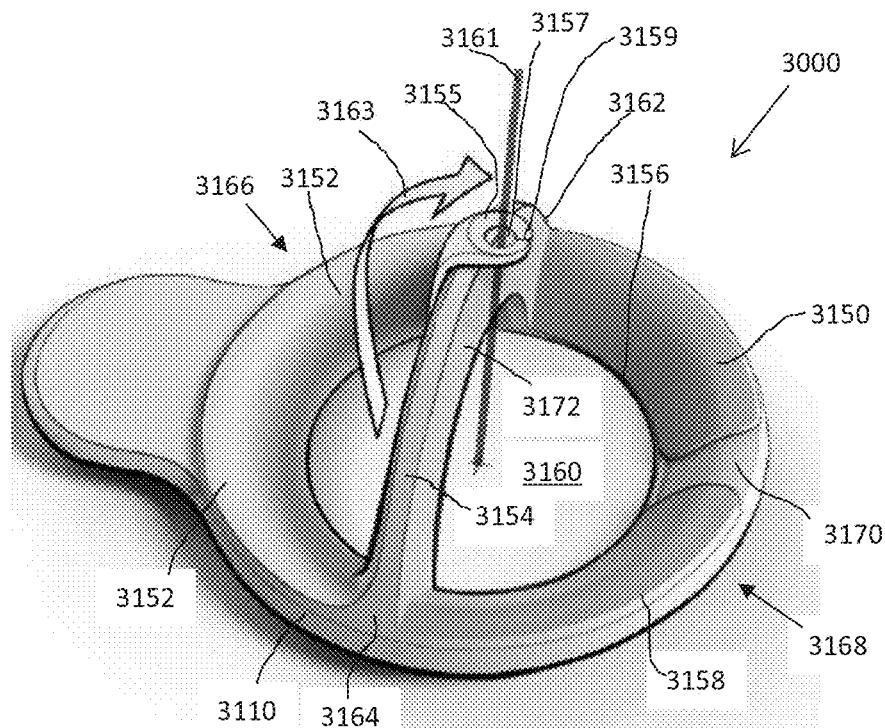
FIG. 10 is a perspective view of another example medical guidance apparatus in accordance with aspects of the disclosure.

FIG. 10 illustrates a perspective view another embodiment of a medical guidance apparatus 3000 having a guide 3150 and a base assembly 3110. The base assembly 3110 and the guide 3150 are similar to the base assembly 110 and guide 150 shown in FIGS. 1-6 and similar reference numbers represent corresponding features. Thus, the base assembly 3110 may similarly include a stationary base ring and a moveable ring. The guide 3150 similarly may include a frame 3152, an arc member 3154, an inner circumference 3156, an outer circumference 3158, an opening 3160, a first end 3162, a second end 3164, a first half 3166, a second half 3168, a gap 3170, a guide surface 3172, and an arc member thickness.

The width of the ring shape of the frame 3152 (i.e., the distance from the inner circumference 3156 to the outer circumference 3158 in a radial direction, which is also the difference between the inner radius and the outer radius of the frame 3152), may be the same as in frame 152. The arc member 3154 may have an arc shape that spans the same angle range as in the arc member 154. The arc member 3154 may be integrally formed with the frame 3152 such that the entire guide 3150 is monolithically formed, as with the guide 150. Thus, the guide 3150 has the same structural advantage as noted above with the guide 150.

Similar to the guide 150, the guide 3150 may be rotatably coupled with the base assembly 3110. The guide 3150 may be coupled via the same mechanical components noted above or with another mechanism. A corresponding feature may be present on the moveable ring or base ring to couple the guide 3150 to the base assembly 3110. The guide 3150 may rotate in the same manner as the guide 150.

As shown in FIG. 10, a difference between the guide 3150 and the guide 150 is that the guide 3150 comprises an instrument holder 3155. The instrument holder 3155 includes a through-hole 3157. The through-hole 3157 may be large enough to loosely hold an instrument 3161. The instrument holder 3155 may further include a slit 3159. The slit 3159 provides a passageway for the instrument 3161 to reach the through-hole 3157 after the instrument has been inserted. The instrument holder 3155 may be made from a material having sufficient flexibility/deformability to allow the slit 3159 to expand when applying force to move the instrument 3161 through the slit 3159. The material should also have sufficient resistance to flexibility/deformability that the slit 3159 returns to the original configuration shown in FIG. 10 when force by the operator is no longer being applied. In this manner, once the instrument 3161 is located in the through-hole 3157, the instrument 3161 will not unintentionally exit the slit 3159.

While not visible in FIG. 10, the side of the arc member 3154 opposite the guide surface 3172 may comprise a rail similar to the rail shown FIG. 9. The rail may have an arc shape along the same arc path defined by the arc member 3154. The instrument holder 3155 may be slideable along the rail along in the same direction shown by arrow 2159 in FIG. 9. The instrument holder 3155 may also be retractable from the arc member 3154 along the arrow 3163 and attachable to the side of the arc member opposite the guide surface 3172. The instrument holder 3155 may be shaped to fit other instruments, depending on the procedure being conducted.

The instrument holder 3155 provides constrained guidance for the instrument 3161. The instrument holder 3155 can accurately guide the instrument 3161 by directing to the target trajectory. With the instrument holder 3155, the instrument 3161 can move freely within the through-hole 3157 without the instrument 3161 falling down even when the operator is no longer holding the instrument 3161. Therefore, the instrument holder 3155 can improve handling management of the instrument 3161 throughout the procedure.

Figure 11:
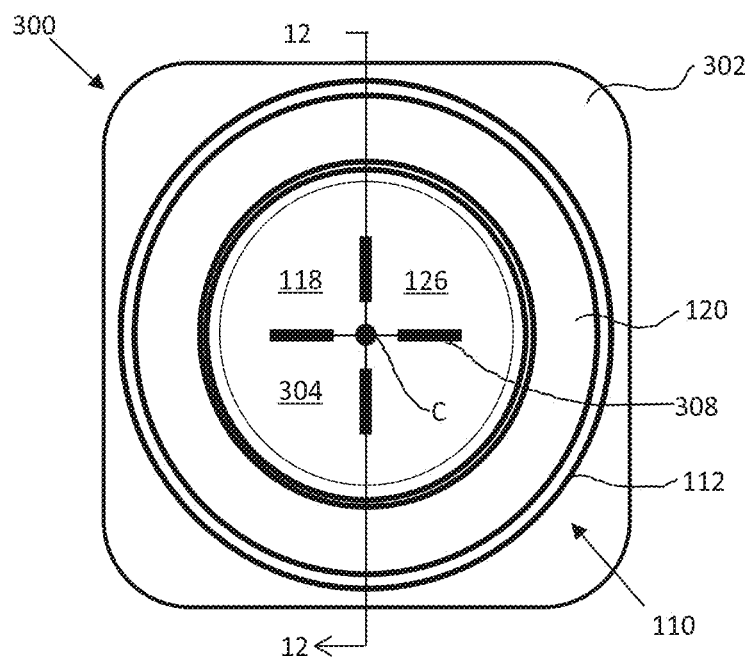
FIG. 11 is top view of the example medical guidance apparatus illustrated in FIG. 1, without a guide and with an adhesive marker.

FIG. 11 illustrates a top schematic view of the base assembly 110, with the guide 150 removed. FIG. 11 illustrates an example embodiment of the base assembly 110, where an adhesive marker 300 has been attached to an underside surface of the base assembly 110. The adhesive marker 300 may include a backing material 302, a peel-away portion 304 aligned with the openings 118, 126, and an adhesive 306. The adhesive 306 may be any known adhesive suitable for use on human skin while having sufficient strength to maintain the position of the medical guidance apparatus on the patient during the procedure. Examples of adhesives are surgical tapes and medical tapes that hold onto the skin but can be removed without damaging the skin. The adhesive marker 300 may be directly attached to the underside surface of the base ring 112. The attachment may be achieved with another layer of adhesive (not shown) on the upper surface 303 of the backing material or any other known attaching mechanism. The adhesive marker 300 may include a center marker 308 located on the peel-away portion 304. As shown in FIG. 11, the center marker 308 may comprise a plurality of lines whose intersection defines a single point, e.g., a cross pattern. The center marker 308 allows the operator to easily align the center point C with the desired entry point on the patient. Other than the center marker 308, the backing material 302 may be transparent.

In some embodiments (not shown), there is also included one or more tabs on the base assembly 110. These tabs are useful, for example, for including additional area for adhesion, where the tabs may have the same adhesive 306 discussed above or an additional adhesive. Alternatively, or in addition, the tabs do not have an adhesive but provide additional support when patient mounted and/or provide a surface for the use of surgical tape or another fixation component to be used to secure the base assembly 110 to the patient. The use of these one or more tabs works in concert with the high rigidity of the monolithic structure. The tabs can be rigidly mounted or may be hinged to allow the device to conform to different anatomies.

Figure 12:
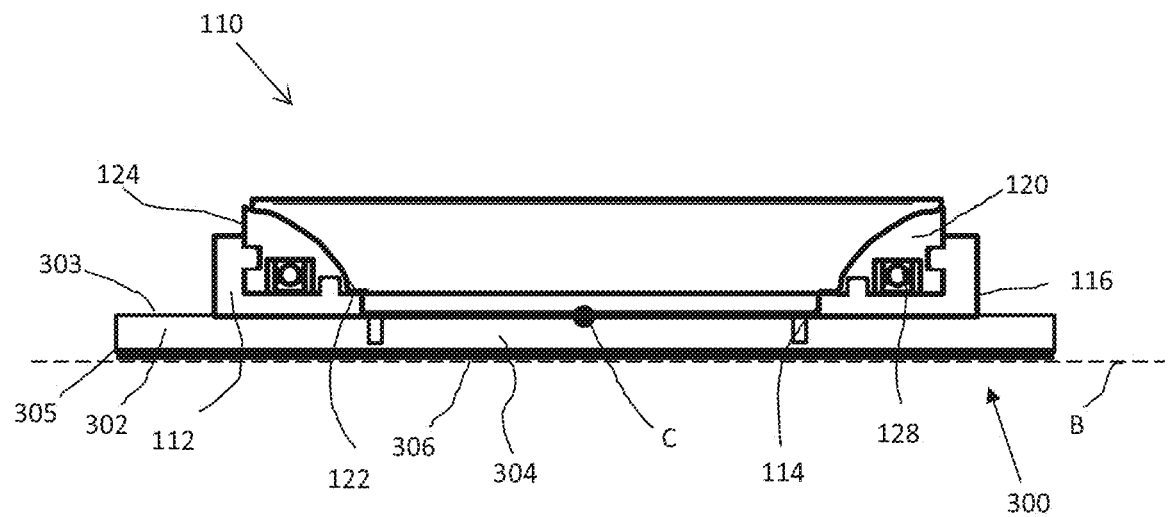
FIG. 12 is a cross sectional view taken along line 12-12 of the example medical guidance apparatus illustrated in FIG. 11, prior to removing a peel-away portion of the adhesive marker.
Figure 13:
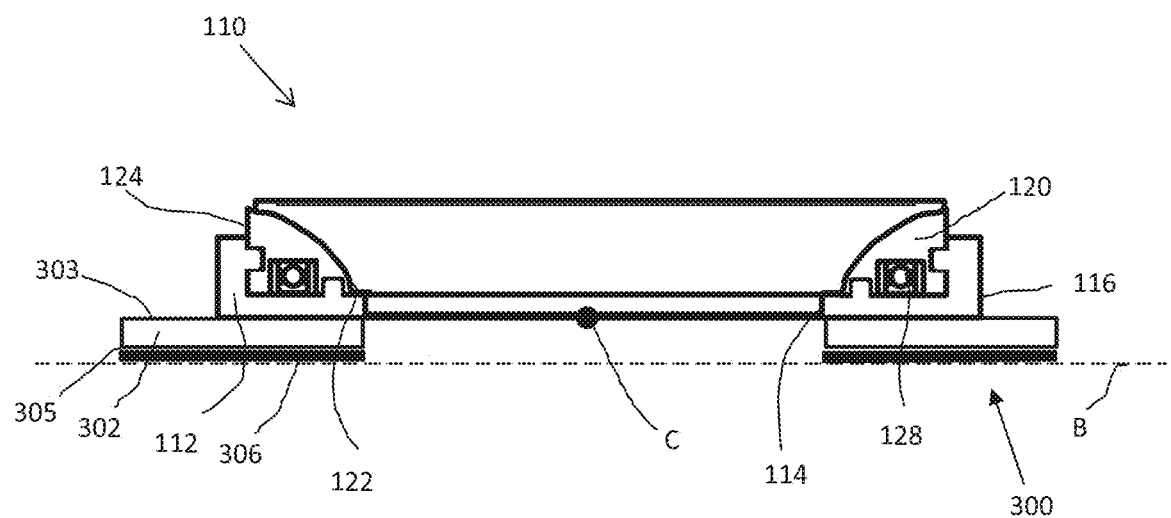
FIG. 13 is a cross sectional view taken along line 12-12 of the example medical guidance apparatus illustrated in FIG. 11, after removing a peel-away portion of the adhesive marker.

FIG. 12 is a cross sectional view taken along line 12-12 of FIG. 11 prior to the removal of the peel-away part 304. FIG. 13 is a cross-sectional view taken along line 12-12 of FIG. 11 after the peel-away portion 304 has been removed. As shown in FIG. 12, the base assembly 110, and more particularly the base ring 112, has the adhesive marker 300 attached to the underside surface. The adhesive 306 extends across the entire underside surface 305 of the adhesive backing material 302, including the peel-away portion 304. In the state shown in FIG. 12, the backing material 302, including the peel-away portion 304, with the adhesive 306, is in contact with the surface B (i.e., the patient's skin), thus fixing the base assembly 110 to the patient. After the operator has aligned the center marker 308 such that the center point C is aligned with the insertion point on the surface B, the operator may peel away the peel-away portion 304, thus exposing the openings 118, 126 to the surface B. The backing material may include a perforation portion (not shown) defining the peel-away portion 304 to allow the operator to peel away the peel-away portion 304. The back material may also include a tab for gripping or any other mechanism to assist in the peeling away the peel-away portion 304. This is the state is shown in FIG. 13, where there is no longer any backing material in the openings of the base ring 112 and the moveable ring 120. The dimensions of the backing material 302 and the adhesive 304 are exaggerated for clarity and it should be understood that the relative dimensions of the base ring 112 and moveable ring 120 are not to scale with the dimension of the backing material 302 and the adhesive 304. That is, in the practice, the thickness (or vertical height in FIGS. 12 and 13) of the backing material 302 and adhesive 304 is several orders of magnitude smaller than the height of the base ring 112 and moveable ring 120 (e.g., micron scale vs centimeter scale). Thus, in practice, the underside of the base ring 112 would essentially be nearly touching the surface B, even with the adhesive marker 300.

It should be understood that the above-described adhesive marker 300 is not a mutually exclusive feature and can be applied to any of the example embodiments described herein. That is, the adhesive marker 300 can be applied to the underside surface of any of the medical guidance apparatuses described herein in order to fix and properly align the base assembly to the operation spot on the patient.

Figure 14:
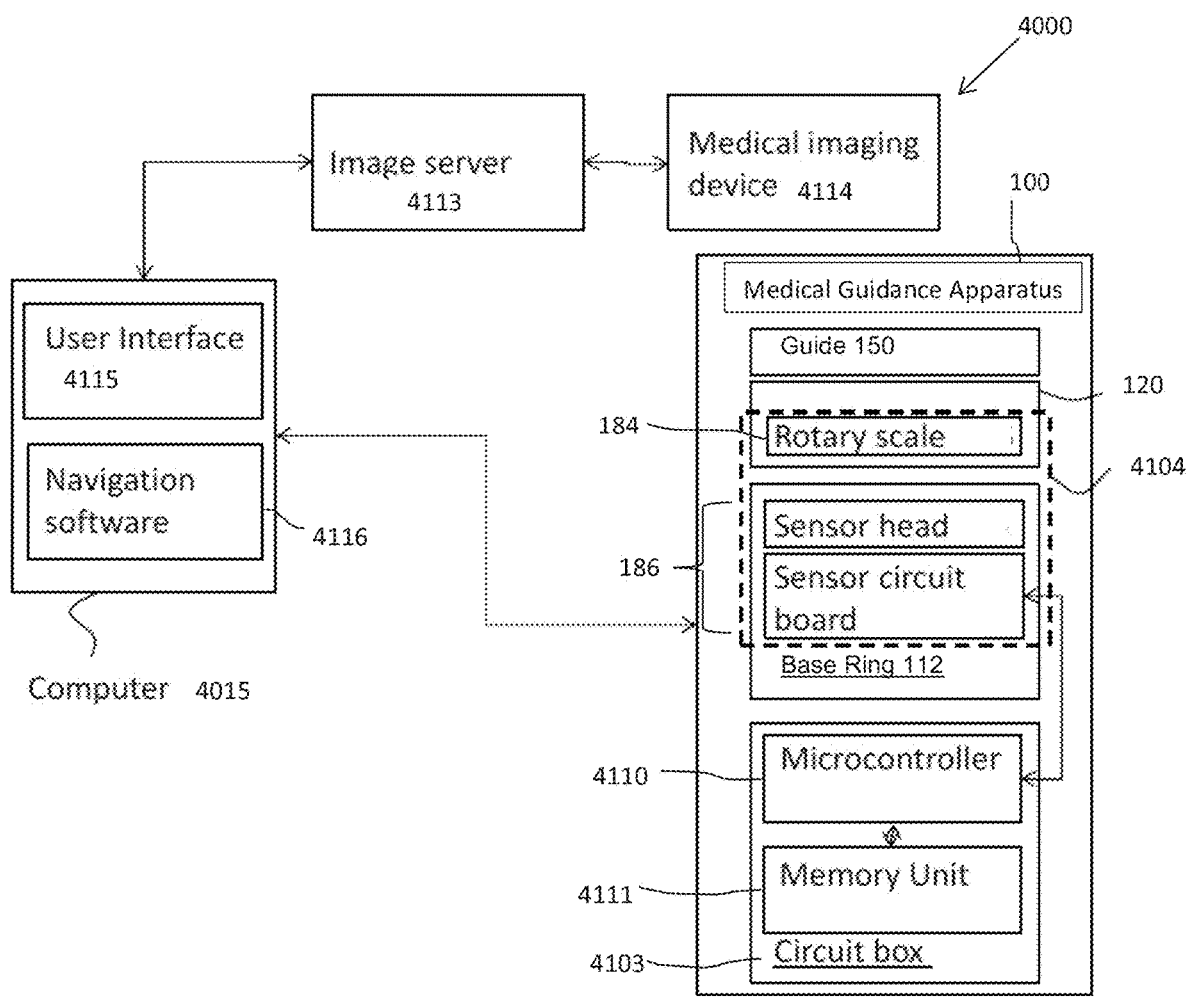
FIG. 14 is a functional block diagram illustrating an example medical guidance system in accordance with aspects of the disclosure.

Turning to the method of using the medical guidance apparatuses 100, 1000, 2000, 3000 described above, FIG. 14 is a functional block diagram illustrating a medical guidance system 4000 according to another embodiment of the present disclosure. For simplicity, reference numbers from the embodiment of the medical guidance apparatus 100 are used hereinafter. However, it should be understood that the following discussion is applicable to all of the example embodiments discussed above. The medical guidance system 4000 transmits and receives data to/from an image server 4113 that receives image information from a medical imaging device 4114. The medical guidance system 400 includes a computer 4015 and a medical guidance apparatus 100 that are communicatively-coupled via a bus. The image server 4113 includes, but is not limited to, a Discom® server or equivalent that receives and stores image information from the medical imaging device 4114. The medical imaging device 114 includes, but is not limited to, a computed tomography (CT) scanner, magnetic resonance imaging (MRI) scanner, positron emission tomography (PET) scanner, single-photon emission computed tomography (SPECT) scanner and/or fluoroscopy scanner.

The computer 4015 of the medical guidance system 4000 includes a user interface 4115 allowing a user to access and control the computer 4015 and navigation software 4116 to determine proper insertion angles of a needle-like medical device into a medical patient based on image data received from the medical imaging device 4114 and stored in the image server 4113. Additionally, the navigation software 4116 provides the operator information including, but not limited to, protocols involving the use of the medical guidance apparatus 100 and visual orientation and location information of the medical guidance apparatus 100.

The base ring 112 may include fiducial markers (not shown) at four corners around the base ring or on/within the grip 113. The fiducial markers are visible optically as well as in CT and X-ray images utilizing radio-opaque material. The radio-opaque material can be, but are not limited to, plastic including fillers of Barium Sulfate, bismuth subcarbonate, bismuth oxychloride, tungsten. At each corner, the fiducial markers form a cluster of markers with different numbers of fiducial markers than each other. Therefore, the position and the orientation of the base ring 112 can be geometrically distinguished using only the fiducial markers and 121D in the CT and X-ray images.

As noted above the axis A passes through point C on the mounting surface B and the angular reference marks 174 are line marks to signify an angle around point C on the guide surface 172. By rotating the moveable ring 120 together with the guide 150 around axis E, the angular reference marks 174 also rotate around axis E. By using the angular reference marks 174, the medical apparatus guide 100 localizes the insertion plane and further localizes fine grids of a remote center of motion with point C. The grids are cone-shaped grids with generator E along the point C as a pivot.

The remote center of motion models an operator's maneuver of a needle-like medical tool. Thus, point C is aligned to a skin entry point of the medical tool, which is defined by considering obstacles close to the patient's skin. With the fixed point C, the operator can select an intended trajectory to the target by using an appropriate position of the moveable ring 120/guide 150 and the angular reference marks 174.

After determining the position of rotatable ring 120 (thereby also the guide 150) and the angular reference marks 174, the operator can insert the needle-like medical tool with guidance from guide 150 at the target angular reference marks 174.

The microcontroller 4110 processes information from the computer 4015 and the sensor circuit board 4107 and the microcontroller 4110 communicates with the computer 4015 and the sensor circuit board 4107 to exchange commands and target information between them. Specifically, the microcontroller 4110 initiates and sends the angular position of the moveable ring 120 measured by the rotary encoder to the computer 4015, as needed.

The microcontroller 4110 is also electrically-connected to the memory unit 4111. The memory unit 4111 stores at least transformation matrices of the medical guidance apparatus 100 based on a local coordinate of the medical guidance apparatus 100, which is determined as design. The microcontroller 4110 then retrieves and sends these transformation matrices in the memory unit 4111 to the computer 4015, when the navigation software 4116 requires them.

Specifically, the circuit box 4103 is electrically-connected to the rotary encoder 4104 at the sensor circuit board 4107 in base ring 112 via the electric cable, as a separate part from the base ring 112. Consequently, the circuit box 4103 in can be placed bedside or near the patient close to an area of the intervention, but separated place from base ring 112. With the circuit box 4103, the base ring 112 can reduce the footprint and reduce the area needed for the intervention. Also, the circuit box 4103 includes an indicator. The indicator reflects the real-time angular position of the moveable ring 120 with a digital indicator. Moreover, the indicator displays different information about the medical guidance apparatus 100, for instance the target angular position of the moveable ring 120, the target angular reference mark, comparison between the target and current angular position of the moveable ring 120, and the remaining battery power. With the indicator on the circuit box 4103, the operator can confirm the information on the medical guidance apparatus 100 on the spot without having to leave the patient and the area of the intervention.

Figure 15:
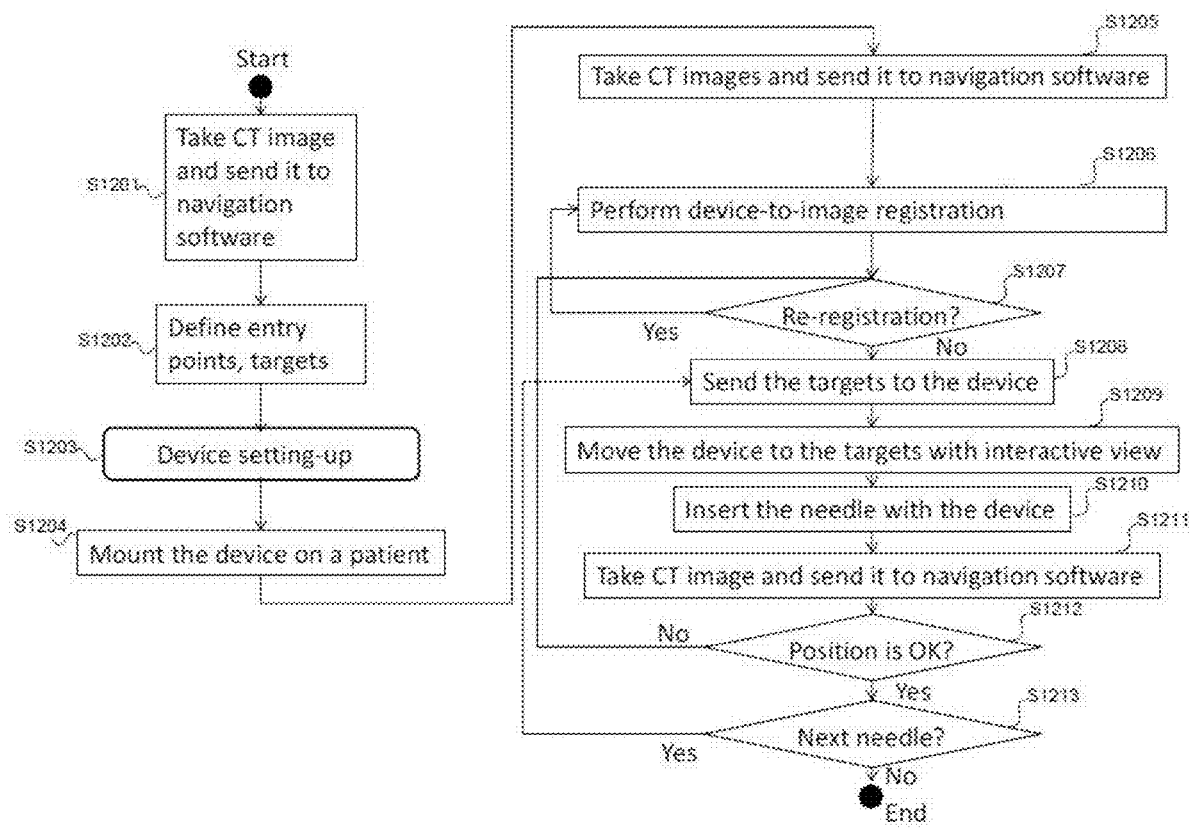
FIG. 15 is a flowchart illustrating a process for guidance of a needle using a medical guidance system accordance with aspects of the disclosure.

FIG. 15 is a flowchart illustrating a process for guidance of a needle using the medical guidance apparatus 4000. In step S1201 an operator takes medical images using the medical imaging device 4114. The medical imaging device 4114 is a CT scanner in this particular embodiment, and sends the CT images to the navigation software 4116 in the computer via the image server 4113.

At step S1202, with the CT images, the operator defines targets for percutaneous intervention with a needle-like medical tool and the skin entry point. At the same time, by connecting the target to the skin entry point, the operator can determine the plane for the trajectory of insertion of the needle-like medical tool using the navigation software 4116. Also, in this step, the operator marks the skin entry point on the patient which is standard practice using for example, grid visible markers on the patient.

In step S1203 the operator sets up the device to calibrate it and sets a proper initial state of the medical guidance apparatus 100. More specifically, setting up the rotary encoder 4104 to establish an original zero position properly.

After the setting up the device, in Step S1204 the operator mounts the medical guidance apparatus 100 onto the patient aligning the point C to the skin entry point. When the adhesive marker 300 is being utilized, the operator may align the center marker 308 to the skin entry point and then adhere the medical guidance apparatus 100 in place via the adhesive 306. The operator then may remove the peel-away portion 304 to expose the patient's skin.

In Step S1205, after the device mounting, the operator takes CT images including the medical guidance apparatus 100 and sends the CT images to the navigation software 4116. Using the CT images with the medical guidance apparatus 100 showing, in Step S1206 the operator conducts device-to-image registration. In this step, the navigation software 4116 recognizes the position and orientation of the medical guidance apparatus 100 on the patient in the CT images, i.e. in the coordinate of the CT image, by using fiducial markers located on the corners of the base ring 112. This fiducial marker detection can be manually performed by operator instruction with user interface or, can be fully automated by using a computer algorithm. The detected fiducial markers are compared with the designed geometrical configuration of the fiducial markers in the medical guidance apparatus 100, then the navigation software can recognize the position and the orientation of the medical guidance apparatus 100 in CT images. The navigation software can also reflect the plan of the trajectory with two device parameters which are angular position of the moveable ring 120 ($\theta_E^F$) and insertion angle on guide 150 ($\theta_E^F$) at this step.

In step S1207, the operator can be asked whether the device-to-image registration is appropriate or not by the navigation software 4116. If not (no is Step S1207), the operator can conduct Step S1206 the device-to-image registration again.

If the device-to-image registration is appropriate (Yes in Step S1207) flow proceeds to Step S1208 where the operator can send the target device parameters $\theta_E^F$, $\theta_P^{MR}$ to the microcontroller 4110.

Afterwards in Step S1209, the operator manually rotates the guide 150 via the moveable ring 120 while the navigation software 4116 interactively updates the cross sectional image on the guide surface by using the real-time angular position of the moveable ring 120 from the microcontroller 4110. Also, the microcontroller 4110 compares the real-time angular position of the moveable ring 120 with the target angular position. Once the moveable ring 120 reaches the target angular position, the microcontroller 4110 informs the navigation software 4116 and indicator 504 of the end of targeting of the moveable ring 120. Then, the navigation software 4116 and/or indicator 504 informs the operator of the end of targeting.

Upon establishing the target angular position of the moveable ring 120 (and thereby the guide 150), in Step S1210 the operator picks the specific angular reference mark 174 indicated by the target insertion angle on guide 150 and with the specific angular reference mark 174, the operator inserts the needle-like medical tool from the skin entry point to the target. In the case of the medical guidance apparatus 100 (FIGS. 1-6), the operator may slide the needle-like medical tool along the guide surface 172 until reaching the appropriate reference mark 174. In doing so the operator may apply force in the direction D. However, due to the structural advantages discussed above provided by the closed/monolithic structure of the guide 150, the arc member 154 is able to fully support the force without deflection or bending. In the case where the guide 1150 (FIG. 8) is being used, the operator will pass the needle-like medical tool through the gap 1157 into the area 1159 between the two arc member components 1155a, 1155b. The operator will then move the needle-like medical tool along the arc shape until arriving at the appropriate marker 1174. The guide surface 1172 also has the structural advantages noted above. In the case where the guide 2150 (FIG. 9) is being used, the operator will pass the needle-like medical tool through the instrument holder 2157. The operator will then move the needle-like medical tool along the rail 2155 via the instrument holder 2157 until arriving at the appropriate marker indicator 2174a (or marker in the case of a marker being present). The guide surface 2172 also has the structural advantages noted above. In the case where the guide 3150 (FIG. 10) is being used, the operator will advance the instrument holder 3155 (if not already advanced) along the direction arrow 3163 the instrument holder 3155 is positioned against the arc member 3154. Next, the operator will pass the needle-like medical tool through the through-hole 3157 of the instrument holder 3155. The operator will then move the needle-like medical tool along the rail via the instrument holder 3155 until arriving at the appropriate marker indicator or marker. The guide surface 3172 also has the structural advantages noted above.

In Step 1211 after the first attempt of the insertion, the operator takes CT images of the inserted needle-like medical tool, the medical guidance apparatus 100, and the CT images and sends them to the navigation software 4116. With the CT images of the inserted needle-like medical tool, the operator evaluates the position of the inserted needle-like medical tool.

In step S1212, the position of the inserted needle-like medical tool is checked and if the operator thinks the position is suboptimal (No in Step S1212), flow proceeds back to Step S1208 where the operator can update the trajectory to improve the position of the needle-like medical tool with navigation software 4116. At the same time, with the latest CT image, the operator finds the dislocation of the target, skin entry point and the medical guidance apparatus 100 and updates the registered position and orientation of medical guidance apparatus 100. Thus, the operator can conduct the device-to-image registration with the latest CT images. By updating the device-to-image registration, the operator can reduce discrepancy of the actual geometrical relationship between the medical guidance apparatus 100 and the target. Specifically, since the medical guidance apparatus 100 is mounted on the patient and can move with the patient body together, the update of the device-to-image registration can effectively compensate rigid dislocation of the patient from the older CT images.

With updated plane of the trajectory and the device-to-image registration, the operator can perform another attempt of the insertion with the same steps as in the first attempt.

In step S1212, if the position of the inserted needle-like medical tool is checked and the operator is satisfied with the results (Yes in Step S1212), flow continues to Step S1213. In Step S1213, a determination is made as to whether insertion of another needle-like medical tool is needed. If insertion of another needle-like medical tool is needed (Yes in Step S1213) flow returns back to Step S1205. If insertion of another needle-like medical tool is not needed (No in Step S1213) flow is complete. When inserting another needle-like medical tool, the operator may decouple the guide 150 from the base assembly 110 as necessary without needing to unmount the base assembly 110. In the case of inserting another needle-like medical tool in one of the guides 2150, 3150, the operator must remove the previous needle-like medical tool from the instrument holder 2157, 3155.

Once all of the needle-like medical tools have been inserted, the operator may decouple the guide 150 from the moveable ring 120. Once the guide 150 has been decoupled and can be freely lifted away, the operator may orient the guide 150 such that each of the needle-like medical tools pass through the gap 170. Thus, the guide 150 is completely removable from the procedure site, even when the needle-like medical tool is tethered, such as for percutaneous ablation probes.

It should be understood that all non-mutually exclusive features shown and discussed with respect to a specific example embodiment may be applied to all other example embodiments. For example, markers may be used in place of illuminators and vice versa for all embodiments, having a different color on the guide surface may be applied to all embodiments, having a grip may be applied to all embodiments, having an adhesive marker may be applied to all embodiments, using an encoder may be applied to all embodiments, etc.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A medical guidance apparatus comprising:
a base assembly including a base ring having an inner circumference defining an opening; and
a guide rotateably mateable with the base assembly, the guide including:
a frame comprising:
an inner circumference defining an opening; and
an outer circumference,
wherein, in a configuration where the guide is mated with the base assembly, the opening of the frame overlays the opening of the base ring;
a gap extending from the inner circumference of the frame to the outer circumference of the frame; and
an arc member including a first end integrally formed with the frame and a second end integrally formed with the frame,
wherein the first end of the arc member is diametrically opposed to the second end of the arc member.

2. The medical guidance apparatus of claim 1, wherein the frame and the arc member are monolithically formed.

3. The medical guidance apparatus of claim 1, wherein the arc member comprises a guidance surface facing the gap.

4. The medical guidance apparatus of claim 3, wherein the guidance surface comprises one or more angular reference marks.

5. The medical guidance apparatus of claim 1, wherein:
the arc member bisects the frame into a first half and a second half,
the first half of the frame is continuous from the first end of the arc member to the second end of the arc member, and
the second half comprises the gap.

6. The medical guidance apparatus of claim 5, wherein the second half of the frame comprises a differentiating marker.

7. The medical guidance apparatus of claim 1, wherein the base assembly further comprises:
a moveable ring having an inner circumference defining an opening; and
a bearing about which the moveable ring is rotatable,
wherein the guide is coupleable with the moveable ring.

8. The medical guidance apparatus of claim 7, wherein the opening of the moveable ring overlays the opening of the frame and the opening of the base ring.

9. The medical guidance apparatus of claim 7, wherein the moveable ring comprises a first tapered portion and the frame comprises a second tapered portion, and wherein the first and second tapered portion are congruent with each other.

10. The medical guidance apparatus of claim 7, wherein the guide is rotatable relative to the base ring about a center point of the opening of the base ring via the coupling with the moveable ring.

11. The medical guidance apparatus of claim 7, wherein the base assembly further comprises a seal configured to prevent contamination from entering the bearing.

12. The medical guidance apparatus of claim 7, wherein the base assembly further comprises a rotary encoder configured to measure an angular position of the moveable ring.

13. The medical guidance apparatus of claim 12, wherein the rotary encoder comprises:
a rotary scale coupled with the moveable ring;
a circuit board and sensor head in electrical communication and coupled with the base ring,
wherein the circuit board is configured to process measurement signals of the angular position of the rotary scale from the sensor head.

14. The medical guidance apparatus of claim 1, further comprising a controller box in electrical communication with the base ring.

15. The medical guidance apparatus of claim 1, further comprising an adhesive marker attached to an underside surface of the base assembly, wherein the adhesive marker comprises a backing material and an adhesive extending across an underside surface of the backing material.

16. The medical guidance apparatus of claim 15, wherein the backing material comprises a peel-away portion aligned with the opening of the base ring.

17. The medical guidance apparatus of claim 15, wherein the adhesive marker further comprises a center marker disposed on the peel-away portion, and wherein the center marker indicates the center point of the opening of the base ring.

18. The medical guidance apparatus of claim 1, wherein the arc member comprises a first arc component and a second arc component, and wherein the first arc component is spaced apart from and opposed to the second arc component.

19. The medical guidance apparatus of claim 1, wherein the guide further comprises:
an instrument holder; and
a rail formed on the arc member,
wherein the instrument holder is slideable along the rail.

20. The medical guidance apparatus of claim 17, wherein the instrument holder is retractable in a direction away from the arc member.

21. A medical guidance apparatus comprising:
a base ring having an inner circumference defining an opening;
a moveable ring having an inner circumference defining an opening, the moveable ring being rotateably coupled with the base ring;

a rotary encoder; and
a guide mateable with the moveable ring, the guide including:
  a frame comprising:
    an inner circumference defining an opening; and
    an outer circumference,
  a gap extending from the inner circumference of the frame to the outer circumference of the frame; and
  an arc member including a first end integrally formed with the frame and a second end integrally formed with the frame,
  wherein, in a configuration where the guide is mated with the moveable ring, the opening of the frame overlays the opening of the base ring and the opening of the moveable ring, and
  wherein the encoder is configured to measure an angular position of the moveable ring.

22. A method of guiding a medical instrument, comprising:
  mounting a medical guidance apparatus onto a predetermined insertion point of a surface, the medical guidance apparatus comprising:
    a base assembly including a base ring having an inner circumference defining an opening; and
    a guide rotateably mateable with the base assembly, the guide including:
      a frame comprising:
        an inner circumference defining an opening; and
        an outer circumference,
        wherein, in a configuration where the guide is mated with the base assembly, the opening of the frame overlays the opening of the base ring;
      a gap extending from the inner circumference of the frame to the outer circumference of the frame; and
      an arc member including a first end integrally formed with the frame and a second end integrally formed with the frame,
      wherein the first end of the arc member is diametrically opposed to the second end of the arc member;
  positioning the guide to a predetermined position relative to the base ring;
  positioning the medical instrument to a predetermined position along the arc member; and
  inserting the medical instrument through the insertion point.

* * * * *